(12) United States Patent
Marshall et al.

(10) Patent No.: US 7,229,432 B2
(45) Date of Patent: Jun. 12, 2007

(54) INJECTION DEVICES

(75) Inventors: Jeremy Marshall, Oxford (GB); Nick Hansen, Oxford (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 10/486,344

(22) PCT Filed: Aug. 8, 2002

(86) PCT No.: PCT/GB02/03643

§ 371 (c)(1),
(2), (4) Date: Aug. 17, 2004

(87) PCT Pub. No.: WO03/013632

PCT Pub. Date: Feb. 20, 2003

(65) Prior Publication Data

US 2004/0267199 A1    Dec. 30, 2004

(30) Foreign Application Priority Data

Aug. 10, 2001  (GB) ................................ 0119520.5

(51) Int. Cl.
*A61M 5/00*    (2006.01)
(52) U.S. Cl. ........................................ 604/110; 604/198
(58) Field of Classification Search ............... 604/187, 604/110, 112, 192, 198, 195, 196, 197, 193, 604/263, 134; 128/919
See application file for complete search history.

(56) References Cited

U.S. PATENT DOCUMENTS 5,478,316 A * 12/1995 Bitdinger et al. ........... 604/135
6,319,233 B1 * 11/2001 Jansen et al. ............... 604/192
6,544,234 B1   4/2003 Gabriel
6,918,889 B1 * 7/2005 Brunel ........................ 604/10
2001/0056263 A1   12/2001 Alchas et al.

FOREIGN PATENT DOCUMENTS

| EP | 0 966 983 | 12/1999 |
|----|-----------|---------|
| FR | 2 794 650 | 12/2000 |
| WO | WO 99/37343 | 7/1999 |
| WO | WO 01 41841 | 6/2001 |
| WO | WO 02/083205 | 10/2002 |

* cited by examiner

*Primary Examiner*—Niccholas Lucchesi
*Assistant Examiner*—Theodore J. Stigell
(74) *Attorney, Agent, or Firm*—Young & Thompson

(57) ABSTRACT

When the injection device is applied to a patient's skin and a plunger is pressed, the entire syringe and a carrier move forwards in relation to a barrel such that ribs on the carrier snap past a rib on a shroud. The syringe is arrested by flanges coming up against the rib, and a spring is compressed and a needle is fully projected. Further pressing on the plunger ejects the dose. The needle shroud is kept at the rearward position by its firm engagement around the injection area. On withdrawal of the device, the shroud is pushed forwards by the spring to protect the needle. This draws fingers through gaps in the ribs, the fingers being forced to bend towards the fingers as the divergence takes effect.

14 Claims, 4 Drawing Sheets

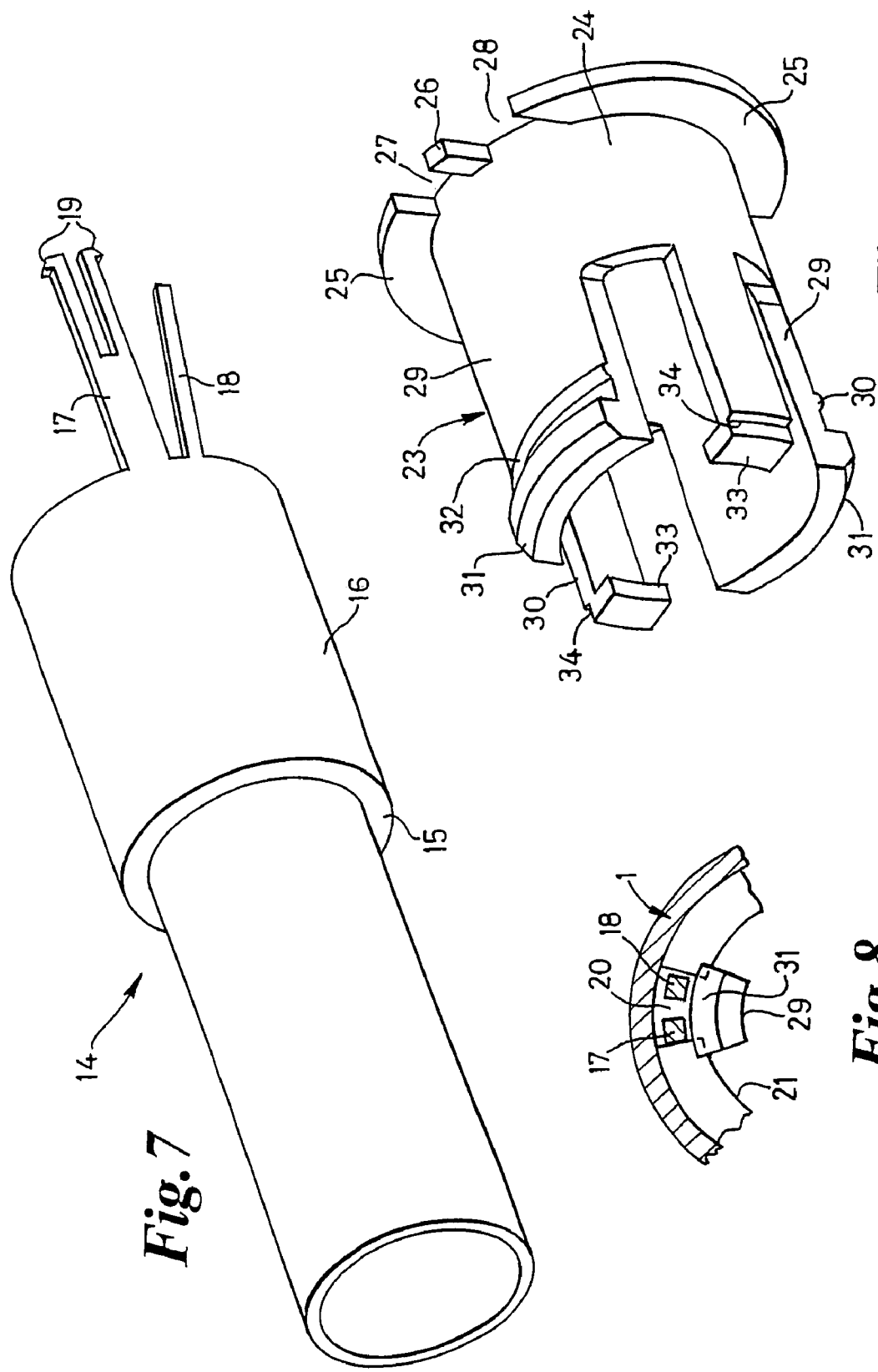

INJECTION DEVICES

Figure 1:
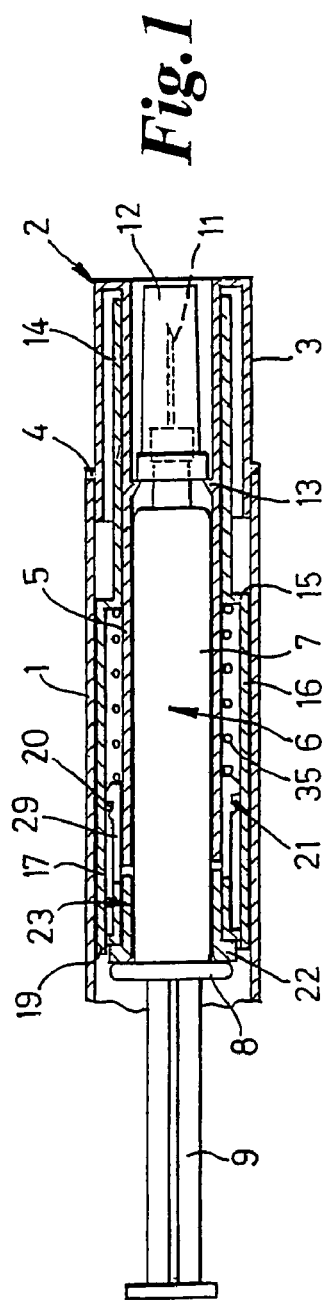

This invention relates to medical injection devices. It is concerned with those in which a syringe is within a housing, initially fully encased, but once the housing is uncapped it can be moved forwards for the needle to be projected and for the dose to be administered. The user holds the housing rather than the syringe itself.

It is known to have a needle shroud carried by the housing which after injection can be shifted to a position concealing the needle. It is important that such a shroud should not then be moved, risking re-exposure of the needle. It is the aim of this invention to provide a simple and reliable way of locking such a shroud automatically to its housing.

According to the present invention there is provided an injection device for a syringe, the device comprising a housing for the syringe with a forwardly biased needle shroud at its leading end capable of movement between forward and rearward positions, the syringe during injection being moved forwards to project its needle beyond the shroud in its rearward position, and the shroud, moved to its forward position concealing the needle after injection, being prevented from reversion to its rearward position by snap-engagement with part of the housing.

Preferably, the shroud will telescope into a barrel-like housing. It can have at least one rearwardly extending finger that extends past an abutment within the housing, that finger being flexed as the shroud moves forwards for its tip to move past the abutment. Thereupon the finger springs back to its natural configuration with its tip in front of the abutment, thereby preventing the shroud moving backwards.

Conveniently, this flexing of the finger will be circumferential, in which case there must be structure for preventing the shroud rotating with respect to the housing if those two members are bodies of revolution. This structure may be combined with structure for preventing complete withdrawal of the shroud from the housing. A further, longer finger may be associated with and divergent from the or each first finger, both fingers of a pair passing through a common gap in the abutment within the housing. This further finger may have a hook formation at its rear, free end, and this will effectively engage behind the abutment when the shroud reaches its forward position. As it moves towards that, the fingers are squeezed together by the sides of the gap until the first, shorter finger clears the gap and springs away from the second, longer finger.

The abutment within the housing may also serve to locate a carrier for the syringe before injection, and it can also provide a limit to the forward movement of the capsule of the syringe.

In the preferred form, the housing will have a cap, removable forwardly for use of the device, with a tubular portion that extends back into the housing to co-operate with the carrier and prevent that disengaging from the abutment. In other words, it keeps the carrier located in its pre-injection position and prevents premature operation. But once the cap is removed, the carrier will be capable of disengagement from the abutment.

Figure 2:
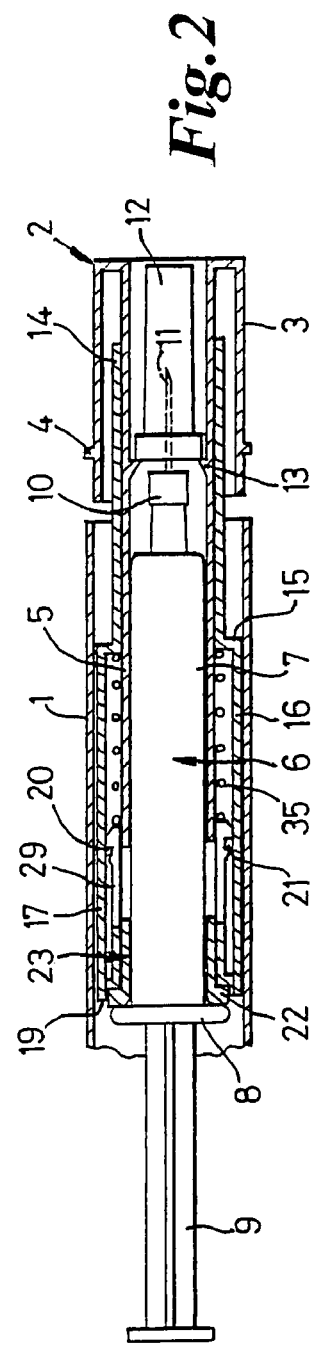
Figure 3:
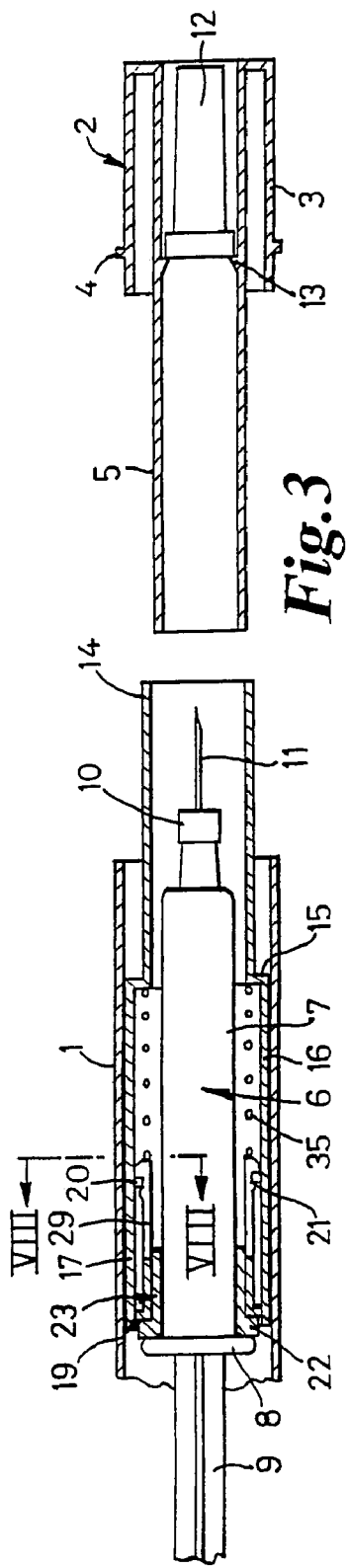
Figure 4:
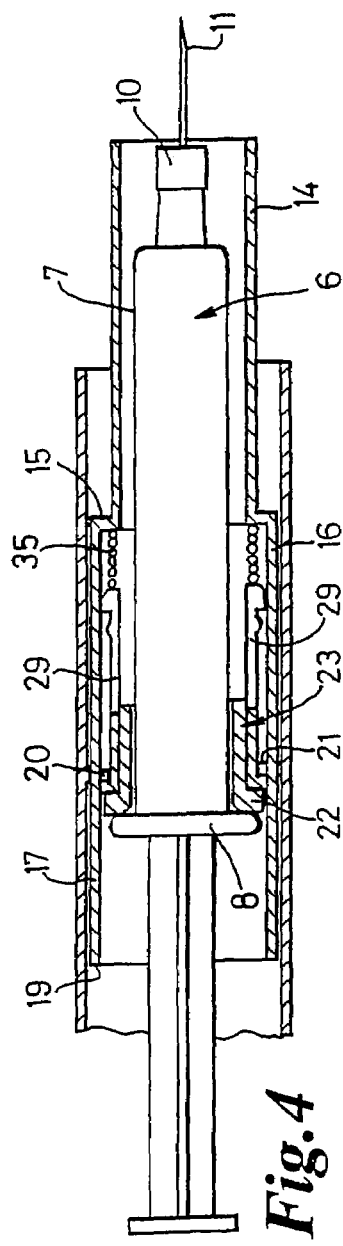
Figure 5:
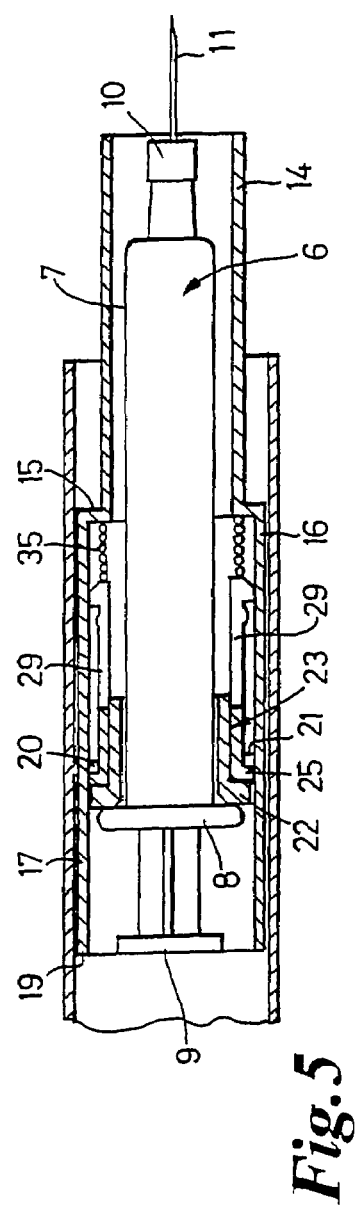
Figure 10:
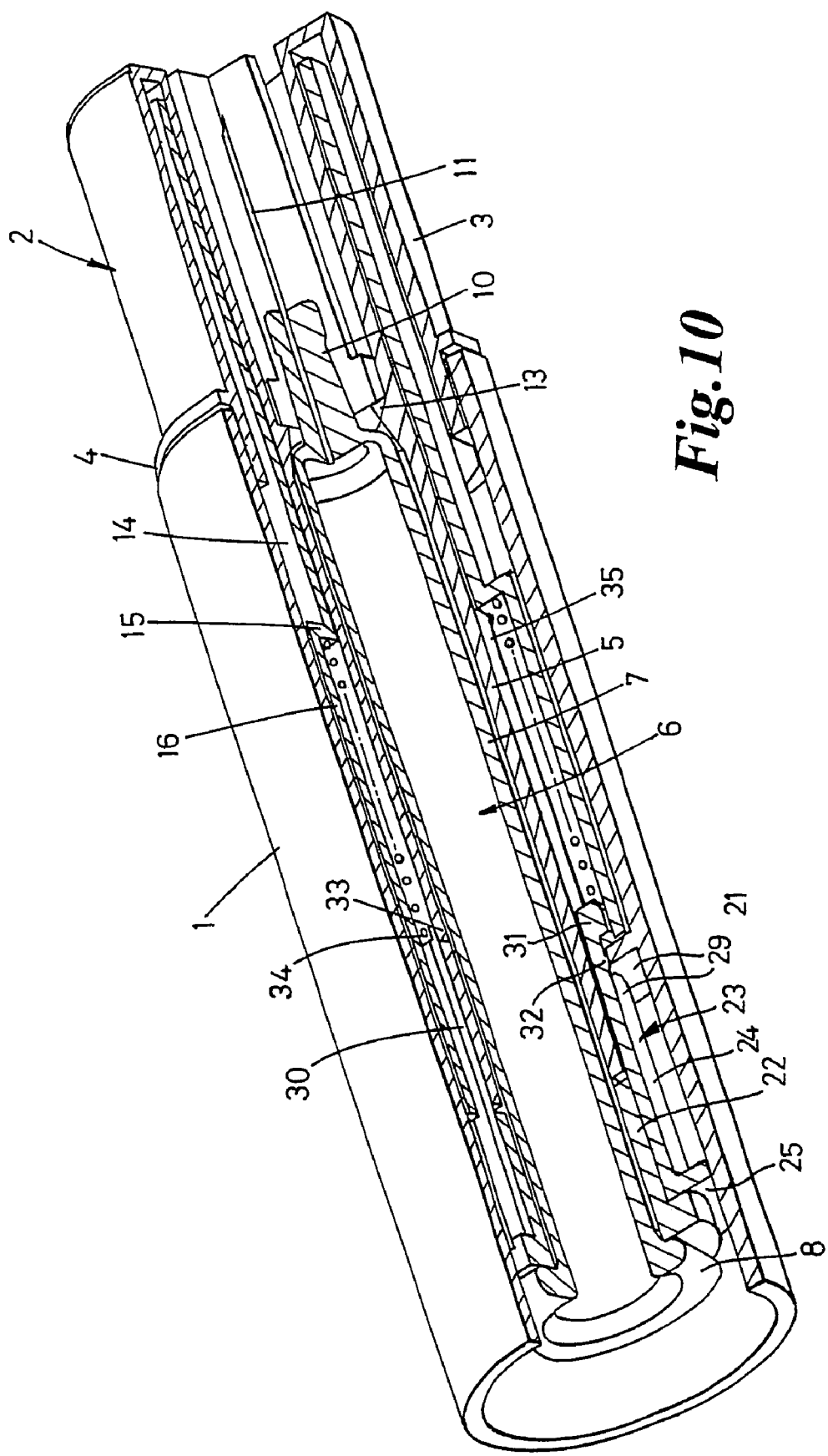

For a better understanding of the invention, one embodiment will now be described, by way of example, with reference to the accompanying drawings, in which:

FIGS. 1 to 6 are axial sections of an injection device showing it in various stages from pre-use to post-use, FIG. 7 is a perspective view of a needle shroud forming part of the injection device, FIG. 8 is a cross-section on the line VIII—VIII of FIG. 3, FIG. 9 is a perspective view of a syringe carrier forming part of the device, and FIG. 10 is a cutaway perspective view of the injection device.

The injection device to be described is intended to form part of an auto-injection system. A spring-loaded drive mechanism will be attached to the rear end of the device, and when released or fired it will act on the syringe within the device to thrust that forward and eject the dose. Such drive mechanisms are known and therefore they are not illustrated and are not described in detail.

The injection device has a cylindrical barrel 1 initially closed at its leading end by an elongate cap 2. This has a relatively short outer tubular section 3 which plugs into the barrel 1, being limited by an annular rib 4, and a much longer re-entrant tubular section 5 which initially extends back into the barrel to encase about three quarters the length of a syringe 6. This is of conventional form with a capsule 7 having a rear end flange 8 beyond which a plunger 9 extends, while at the reduced leading end there is a needle assembly 10 with the needle 11 concealed within a sheath 12. The interior of the re-entrant portion 5 has an annular rib 13 of triangular section which, on assembly, can snap past the enlarged base of the sheath and engage behind it.

Surrounding the forward half of the re-entrant portion 5 in the initial state of the device is a tubular needle shroud 14. This steps out at a shoulder 15 into a short rear tubular section 16, from whose free rim there project rearwardly two pairs of fingers 17 and 18, one of which is best seen in FIG. 7. The finger 17 is the longer, is axially parallel, and terminates at its rear end in a bifurcation with outwardly projecting barbs 19. The shorter finger 18 has a plain end, and it diverges circumferentially slightly from the finger 17. Initially, both these pairs of fingers extend through diametrically opposed gaps 20 in an annular rib 21 on the inside of the barrel 1, as shown in the detail of FIG. 8. The plastics material of which the needle shroud 14 is made allows the fingers 18 to be flexed towards the associated fingers 17, to allow them to pass through the gaps 20 on assembly.

Surrounding the rear end of the capsule 4, with the intermediary of a resilient bush 22, there is a syringe carrier 23, as best seen in FIG. 9. This has a short cylindrical portion 24 with two outward almost semi-circular flanges 25 at its rear end between whose ends there are studs 26 creating gaps 27 and 28. Two pairs of diametrically opposed fingers 29 and 30 project from the forward end of the portion 24, the fingers 29 being wider in the circumferential direction than the gaps 20 and externally terminating in angle teeth 31 with a rounded rib 32 a short distance to the rear of each tooth 31. The bevel or angle on the forward side is to aid assembly, when the teeth are snapped past the rib 21. The fingers 30 of the other pair are somewhat narrower, slightly longer, and terminate in inward flanges 33 with a rebate 34 in the outside of each corner between finger 30 and flange 33. The radial faces of these rebates 34 are co-planar with the ends of the fingers 29. A helical spring 35 has its rear end located by these rebates 34 and also bears against the ends of the fingers 29 while its forward end acts against the shoulder 15. As assembled, the fingers 29 and 30 overlap the rear end of the re-entrant portion 5, and the teeth 31 and ribs 32 engage around the rib 21 on either side of the gaps 20. The ends of the fingers 17 extend through the gaps 27 and their barbs 19 hook behind the flanges 25 and studs 26 of the syringe carrier 23. The tips of the fingers 18 are opposite the gaps 28 and the spring 35 is relaxed.

To prepare the device for use, the cap 2 is removed as shown in FIGS. 2 and 3. By virtue of the rib 13 engaging behind the sheath 12, that is drawn off the needle 11. During the initial freeing of the sheath 12 the rear end of the portion 5 still overlaps the fingers 29, thereby preventing them from flexing inwards and keeping the ribs 32 engaged with the rear side of the rib 21. The carrier 23 is not therefore tugged forwards with the sheath 12. But once that sheath is freed from the needle assembly 10, the internal backing of the fingers 29 by the portion 5 is no longer there, making it possible for those fingers to flex inwardly.

Also initially, the needle shroud 14 cannot move backwards because the rear end of the portion 16 is up against the rib 21, and it cannot move forwards since the barbs 19 are hooked behind the flanges 25 and studs 26 of the immobilised syringe carrier 23.

The device is then applied to the patient's skin and the plunger 9 pressed. This pushes the entire syringe and the carrier 23 forwards in relation to the barrel 1 by virtue of the effective solidity of the dose within the capsule, the ribs 32 snapping passed the rib 21 at the commencement of this movement. The syringe is arrested by the flanges 25 coming up against the rib 21, the spring 35 now being compressed and the needle 11 fully projected. Further pressing on the plunger 9 ejects the dose. The needle shroud 14 is kept at its original rearward position by its firm engagement around the injection area.

Figure 6:
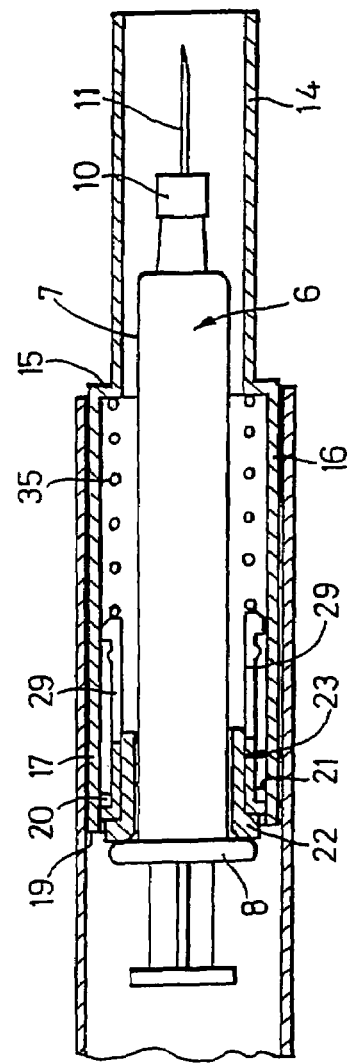

On withdrawal of the device, the needle is protected by the shroud 14 being pushed forwards by the spring 35 to the position shown in FIG. 6. This draws the fingers 17 and 18 through the gaps 20, the fingers 18 being forced to bend towards the fingers 17 as the divergence takes effect. But once the fingers 18 have passed the rib 21, they spring back to their natural straight condition. This means that they will abut the rib 21 if any attempt is made to push the shroud 14 backwards again. At the same time the barbs 19 re-engage the rear end of the syringe carrier 23 whose flanges 25 are up against the rib 21, thus thwarting any attempt that may be made to pull the needle shroud clear of the barrel. The shroud 14 is therefore trapped, the needle 11 safely within.

The invention claimed is:

1. An injection device for a syringe, the device comprising a housing for the syringe with a forwardly biased needle shroud at the leading end of the housing, the needle shroud being capable of movement between forward and rearward positions, the shroud being non-rotatably mounted relative to the housing, the syringe during injection being moved forwards relative to the housing to project a needle of the syringe beyond the shroud, when said shroud is in said rearward position, wherein the shroud has at least one rearwardly extending finger that extends past an inwardly projecting abutment within the housing, that finger being flexed in a circumferential direction as the shroud moves from the rearward position to the forward position under said forward bias, for a tip of the finger to move past the abutment, the finger being located to spring back to a natural configuration with said finger tip in front of the abutment, thereby to prevent the shroud moving backwards, after the shroud has returned to the forward position.

2. An injection device according to claim 1, wherein the shroud telescopes into a barrel-like housing.

3. An injection device according to claim 1, wherein an anti-rotation engagement is combined with structure for preventing complete withdrawal of the shroud from the housing.

4. An injection device according to claim 3, wherein a further, longer finger is associated with and divergent from the or each first finger, the first and further fingers of the pair passing through a common gap in the abutment within the housing.

5. An injection device according to claim 1, wherein the abutment within the housing serves to locate a carrier for the syringe before injection.

6. An injection device according to claim 5, wherein the abutment within the housing provides a limit to forward movement of the capsule of the syringe.

7. An injection device according to claim 5, wherein the housing has a cap, removable forwardly for use of the device, with a tubular portion that extends back into the housing to co-operate with the carrier and prevent the carrier disengaging from the abutment.

8. An injection device according to claim 1, wherein a further, longer finger is associated with and divergent from the or each first finger, the first and further fingers of the pair passing through a common gap in the abutment within the housing.

9. An injection device for a syringe, the syringe comprising a housing for the syringe with a forwardly biased needle at the leading end of the housing, the needle shroud being capable of movement between forward and rearward positions, the syringe during injection being moved forward relative to the housing to project a needle of the syringe beyond the shroud when said shroud is in said rearward position, wherein the shroud has at least one rearwardly extending finger that extends past an inwardly projecting abutment within the housing, that finger being flexed as the shroud moves from the rearward to the forward position under said forward bias, for a tip of the finger to move past the abutment, the finger being located to spring back to a natural configuration with a tip of the finger in front of the abutment thereby preventing the shroud moving backwards, after the shroud has returned to its forward position, the device including a further, longer finger associated with and divergent from the or each first finger, the first and further fingers of the pair passing through a common gap in the abutment within the housing.

10. An injection device according to claim 9, wherein the further finger has a hook formation at a rear, free end of said further finger, which will engage behind the abutment when the shroud reaches said forward position.

11. An injection device according to claim 9, wherein flexing of the or each first finger is circumferential.

12. An injection device for a syringe, the device having a forward end and a rearward end, and comprising:
a housing (1) for a syringe (6) having a needle (11),
a syringe carrier (23) mounting said syringe (6) in said housing for sliding movement between a rearward and a forward position,
a forwardly-biased needle shroud (14) mounted at the forward end of said housing for relative, movement between said forward and rearward positions,
the syringe (6) being moveable forwardly relative to the housing (1) during injection to project said needle (11) beyond the shroud (14) when the shroud is in said rearward position, wherein the shroud has at least one rearwardly extending finger (18) that extends past an inwardly projecting abutment (21) in the housing (1), that finger (18) being flexed in a circumferential direction as the shroud (14) moves from the rearward to the forward position under said forward bias (35), for a tip of the finger to move past the abutment (21), the finger (18) being located to spring back to a natural configuration with the finger tip in front of the abutment (21) thereby preventing the shroud (14) moving backwards after the shroud has returned to the forward position and wherein said shroud is non-rotatably mounted with respect to said housing.

13. An injection device according to claim 12, wherein said housing and said syringe are disposed such that said needle is prevented from forward movement relative to said housing following said non-return snap-engagement between the shroud and the housing.

14. An injection device for a syringe, the device having a forward end and a rearward end, and comprising:
- a housing (1) for a syringe (6) having a needle (11),
- a syringe carrier (23) mounting said syringe bracket (6) in said housing for sliding movement between a rearward and a forward position,
- a forwardly biased needle shroud (14) mounted at the forward end of the housing for relative movement between said forward and rearward positions,
- the syringe (6) being moveable forwardly relative to the housing (1) during injection to project said needle (11) beyond the shroud (14) when the shroud is in said rearward position, wherein the shroud has at least one rearwardly extending finger (18) that extends past an inwardly projecting abutment (21) in the housing (1), that finger (18) being flexed as the shroud (14) moves from the rearward to the forward position under said forward bias (35), for a tip of the finger to move past the abutment (21), the finger (18) being located to spring back to a natural configuration with said tip in front of the abutment (21) thereby preventing the shroud (14) moving backwards after the shroud has returned to the forward position, the device including a further, longer finger (17) associated with and divergent from the or each first finger (18), the first and further fingers (18, 17) passing through a common gap (20) in the abutment (21) within the housing.

* * * * *